(12) United States Patent
Bauer et al.

(10) Patent No.: US 6,630,492 B1
(45) Date of Patent: Oct. 7, 2003

(54) LYMPHOCYTE FUNCTION ANTIGEN-1 ANTAGONISTS

(75) Inventors: Wilfried Bauer, Lampenberg (CH); Sylvain Cottens, Witterswil (CH); Dieter Geyl, Heitersheim (DE); Gabriele Weitz-Schmidt, Bad Krozingen (DE); Jörg Kallen, Basel (CH); Ulrich Hommel, Müllheim (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/486,244

(22) PCT Filed: Aug. 26, 1998

(86) PCT No.: PCT/EP98/05415

§ 371 (c)(1),
(2), (4) Date: Feb. 24, 2000

(87) PCT Pub. No.: WO99/11258

PCT Pub. Date: Mar. 11, 1999

(30) Foreign Application Priority Data

Aug. 28, 1997 (GB) ............................................... 9718157
Mar. 25, 1998 (GB) ............................................... 9806413

(51) Int. Cl.[7] ................. A61K 31/351; A61K 31/4412; C07D 211/86; C07D 319/06; C07D 407/10
(52) U.S. Cl. ................. 514/354; 514/452; 514/460; 546/285; 549/228; 549/273
(58) Field of Search ................. 514/354, 452, 514/460; 546/285; 549/228, 273; 560/125, 126

(56) References Cited

U.S. PATENT DOCUMENTS

| | | |
|---|---|---|
| 4,611,081 A | 9/1986 | Lynch et al. |
| 4,665,091 A | 5/1987 | Hoffman |
| 4,678,806 A | 7/1987 | Baldwin et al. |
| 4,876,366 A | 10/1989 | Hoffman et al. |
| 5,072,002 A | 12/1991 | Clive et al. |
| 5,075,327 A | 12/1991 | Tang et al. |
| 5,116,870 A | 5/1992 | Smith et al. |
| 5,620,876 A | 4/1997 | Davis et al. |
| 6,355,664 B1 | 3/2002 | Kelly et al. ................. 514/389 |

FOREIGN PATENT DOCUMENTS

| | | |
|---|---|---|
| EP | 033 527 | 8/1981 |
| EP | 245 003 | 11/1987 |
| EP | 605 230 | 7/1994 |

OTHER PUBLICATIONS

Dansette et al., "HMG-CoA Reductase Activity in Human Liver Microsomes: Comparative Inhibition by Statins", Exp. Toxic Pathol., vol. 52, pp. 145–148 (2000).
Kremers et al., "Cytochrome P–450 Monooxygenase Activities in Human and Rat Liver Microsomes", Eur. Y. Biochem., vol. 118, pp. 599–606 (1981).
Di Napoli, P. and Barsotti A., Circulation, vol. 97, No. 9, p. 937 (1998).
Wenke, K. et al., Circulation, vol. 96, No. 5, pp. 1398–1402 (1997).
Niwa, S. et al., Int. J. Immunopharmac., vol. 18, No. 11, pp. 669–675 (1996).
Reichart, B. et al., Kidney International, vol. 48, Suppl. 52, pp. S–52–S–55 (1995).
Chen, G–Z et al., Naunyn–Schmiedeberg's Arch Pharmacol, vol. 342, pp. 477–482 (1990).

*Primary Examiner*—Taofiq Solola
(74) *Attorney, Agent, or Firm*—Thomas R. Savitsky

(57) ABSTRACT

Mevinolin compounds for use in the treatment or prevention of autoimmune diseases, inflammation, ischemia/reperfusion injury and graft rejection. Such compounds bind to the LFA-1 I-domain and thereby inhibit LFA-1/ICAM-1 or LFA-1/ICAM-3 interactions.

11 Claims, No Drawings

LYMPHOCYTE FUNCTION ANTIGEN-1 ANTAGONISTS

The present invention relates to compounds which bind to all or parts of the active binding "south pole pocket" of the LFA-1 I-domain and their uses as LFA-1 antagonists.

The lymphocyte function associated antigen LFA-1 belongs to the β2-integrins and plays an important role in T-cell activation and extravasation. Interactions of LFA-1 with its counter-receptors on endothelial and antigen presenting cells such as ICAM-1 or ICAM-3 are an important process in leucocyte endothelial cellular adhesion and migration which mediates disorders or diseases, e.g. auto-inmuune diseases, inflammation, ischemia/reperfusion injury and graft rejection after transplantation.

The so-called I-domain (Inserted Domain) of LFA-1 comprises a module of about 190 amino acids (Takada et al., Matrix Biology, 16, 143–151, 1997). The I-domain folds into a common structural motif comprising a central β-sheet surrounded by helices as determined by X-ray crystallography. (A. Qu & D. Leahy, Proc. Natl. Acad. Sci. USA, 92, 10277–10281, 1995).

Compactin and Mevinolin are fungal metabolites which have following formula:

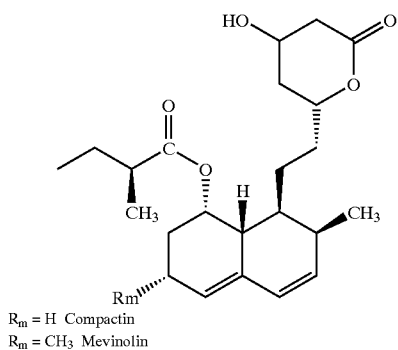

$R_m$ = H Compactin
$R_m$ = $CH_3$ Mevinolin

They are disclosed e.g. by Y. Chapleur in "Progress in the Chemical Synthesis of Antibiotics and Related Microbial Products", Springer Verlag, 1993, vol. 2, 829–937.

Mevinolin and most of the known analogues, e.g. pravastatin, mevastatin, simvastatin etc. have been found to be useful e.g. as 3-hydroxy-3-methyl glutaryl coenzyme A reductase (HMG CoA R) inhibitors.

In accordance with the present invention, it has now surprisingly been found that mevinolin and derivatives thereof bind to LFA-1. Accordingly, the invention provides compounds for use in the treatment or prevention of autoimmune diseases, inflammation, ischemia/reperfusion injury and graft rejection which are preferably specific or substantially specific LFA-1 binding molecules, e.g. specific or substantially specific inhibitors of LFA-1/ICAM-1 or ICAM-3 interactions. Such compounds are preferably other than LFA-1 antibodies.

More particularly, it has been found that mevinolin binds to the LFA-1 I-domain between the C-terminal helix α7 and one side of the β-sheet (hereinafter the "south pole pocket"). X-ray analysis of the complex of LFA-1 I-domain with mevinolin shows that mevinolin does not bind to the MIDAS-site ("metal ion dependent adhesion site").

The complex, LFA-1 I-domain/mevinolin, is prepared by adding mevinolin (100 mM solution in DMSO) to the protein solution (12.7 mg/ml, 100 mM $MgSO_4$), followed by crystallization. The structure is solved by molecular replacement (using the coordinates of apo LFA-1 I domain, A. Qu & D. Leahy, above) and has been refined to a R factor of 19.4% ($R_{free}$=25.9%) using X-ray amplitudes in the resolution range 8 Å–2.6 Å. The final model contains 2×182 amino acids (amino acid residues 128 to 309 of the α-chain of LFA-1 which corresponds to the I-domain), 2 mevinolin molecules and a total of 86 water molecules.

| Data collection statistics | |
|---|---|
| | LFA-1 I-domain/Mevinolin |
| Temperature | 293K |
| Wavelengh | 1.5418Å |
| Resolution range | 15.0Å–2.60Å |
| Spacegroup | $P2_12_12_1$ |
| Unit cell dimensions | a = 72.7Å, b = 77.7Å, c = 91.8Å |
| Measurements used | 87179 |
| Unique reflections | 16457 |
| Completeness | 99.9% (99.8% in shell 2.69Å–2.60Å) |
| Multiplicity | 5.3 (5.2) |
| Average I/sig(I) | 13.9 (2.1) |
| Rmerge | 11.6% (48.4%) |

The south pole pocket is a cavity between one side of the central β-sheet (amino acids of $β_1$, $β_3$, $β_4$, $β_5$, preferably the side chains of such amino acids) and the α-helices $α_1$, $α_7$ (secondary structure of LFA-1 I-domain). Preferably the south pole pocket is the cavity defined by amino acids Val 130, Leu 132, Phe 134, Phe 153, Val 157, Leu 161, Tyr 166, Thr 231, Val 233, Ile 235, Ile 255, Tyr 257, Ile 259, Lys 287, Leu 298, Glu 301, Leu 302, Lys 305, particularly Leu 132, Phe 153, Val 157, Val 233, Ile 235, Tyr 257, Ile 259, Lys 287, Leu 298, Glu 301, Leu 302, Lys 305 of LFA-1 I-domain, more particularly by the side chains of such amino acids. In this pocket, the non-hydrogen atoms of mevinolin preferably interact within a distance of <5 Å, particularly 4–4.5 Å.

The complex south pole pocket/mevinolin is energetically favored by hydrophobic, van der Waals and/or electrostatic interactions and possibly also by indirect hydrogen bonding.

As it will be appreciated, there are 2 complexes LFA-1 I-domain/mevinolin per asymemetric unit which are related by a non-crystallographic two fold axis.

As a result of its shape the south pole pocket as defined above favorably associates not only with mevinolin but with other chemical entities or ligands. Such entities or compounds are LFA-1 inhibitors or LFA-1/ICAM-1 or ICAM-3 interaction inhibitors.

The present invention provides any chemical entity or ligand, which binds in whole or in part to the south pole pocket of LFA-1 I-domain as defined above. Preferably the chemical entity or ligand interacts within a distance <5 Å, particularly 4–4.5 Å. Suitable examples of such chemical entities include e.g. mevinolin derivatives. The elucidation of the mevinolin binding interactions on the LFA-1 I-domain south pole pocket provides the necessary information for designing new chemical entities and compounds that may interact in whole or part with the south pole pocket. Thus, the present invention permits the use of molecular design techniques e.g. computer modeling techniques, as a means of identifying, selecting and designing chemical entities or compounds capable of binding to the south pole pocket.

The design of compounds that bind to the south pole pocket according to the invention generally involves consideration of two factors. First, the entity must be capable of physically and structurally associating with parts or all of the south pole pocket. Non-covalent molecular interactions important in this association include hydrophobic, van der Waals interactions, hydrophobic interactions and/or electrostatic interactions and possibly also hydrogen bonding.

Second, the entity must be able to assume a conformation that allows it to associate with the south pole pocket directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the south pole pocket, or the spacing between functional groups of an entity comprising several chemical entities that directly interact with the south pole pocket.

The chemical entities which interact in whole or in part with the south pole pocket, preferably in a way similar to that of mevinolin may further be tested for their ability to inhibit LFA-1/ICAM-1 or ICAM-3 interactions, using the Jurkat or Hut 78 cell assay described below under A). Representative compounds which bind to the south pole pocket according to the invention are those which inhibit the adhesion of Jurkat or Hut 78 cells to ICAM-1 with an $IC_{50} \leq 30$ μM. These compounds are indicated as LFA-1 antagonists or LFA-1/ICAM-1 or ICAM-3 interaction inhibitors.

Preferred compounds of the invention for use in accordance with the invention are mevinolins (hereinafter referred to as "mevinolins of the invention"), preferably those having no or only limited HMG CoA R inhibitory activity.

Accordingly, the invention provides:

1. A compound for use in the treatment and/or prevention of autoimmune diseases, acute or chronic inflammatory diseases, ischemia/reperfusion injury, acute or chronic rejection of organ or tissue allo- or xenografts or infection diseases by virtue of its LFA-1 inhibitory activity.

1.1 A compound for use in the treatment and/or prevention of autoimmune diseases, acute or chronic inflammatory diseases, ischemia/reperfusion injury, acute or chronic rejection of organ or tissue allo- or xenografts or infection diseases, the compound binding in whole or in part to the south pole pocket, e.g. as defined above, e.g. with an interaction at a distance <5 Å, preferably 4–4.5 Å.

1.2 Mevinolins for use in the treatment and/or prevention of autoimmune diseases, acute or chronic inflammatory diseases, ischemia/reperfusion injury, acute or chronic rejection of organ or tissue allo- or xenografts or infection diseases, by virtue of their LFA-1 inhibitory activity.

1.3 Mevinolins for use in the treatment and/or prevention of autoimmune diseases, acute or chronic inflammatory diseases, ischemia/reperfusion injury, acute or chronic rejection of organ or tissue allo- or xenografts or infection diseases, which bind in whole or in part to the south pole pocket, e.g. as defined above, e.g. with an interaction at a distance <5 Å, preferably 4–4.5 Å.

1.4 Mevinolins for use in the treatment and/or prevention of autoimmune diseases, acute or chronic inflammatory diseases, ischemia/reperfusion injury, acute or chronic rejection of organ or tissue allo- or xenografts or infection diseases, according to 1.2 or 1.3, which inhibit HMG CoA R activity with an $IC_{50} \geq 1$ μM in the In Vitro Microsomal Assay of HMG CoA R Inhibition as disclosed below.

2. A method for producing a chemical entity or ligand which associates with the LFA-1 I-domain south pole pocket comprising the steps of:

a. employing computational means to perform a fitting operation between the chemical entity and the south pole pocket; and
   b. analyzing the results of said fitting operation to quantify the association between the chemical entity and the south pole pocket.

In Vitro Microsomal Assay of HMG-CoA Reductase Inhibition

200 μl aliquots (1.08–1.50 mg/ml) of rat liver microsomal suspensions, freshly prepared from male Spargue-Dawley rats (150–225 g body weight), in Buffer A with 10 mmol dithiothreitol are incubated with 10 μl test substance dissolved in dimethylacetamide and assayed for HMG CoA R activity as described by Ackerman et al., J Lipid Res. 18, 408–413 (1977). In the assay the microsomes are the source of the HMG CoA R enzyme which catalyses the reduction of HMG CoA R to mevalonate. The assay employs a chloroform extraction to separate the product, [$^{14}$C] mevalonolactone, formed by the HGM CoA R reaction from the substrate, [$^{14}$C]HMG-CoA. [$^{3}$H]mevalono-lactone is added as an internal reference. Inhibition of HMG CoA R is calculated from the decrease in specific activity [$^{14}$C/$^{3}$H] mevalonate of test substances compared to controls and is expressed as $IC_{50}$ (concentration of test substance which inhibits 50% of HMG CoA R activity).

The utility of the compounds of the invention, e.g. the mevinolins of the invention as inhibitors of LFA-1/ICAM-1 or ICAM-3 interactions may be demonstrated in following test methods:

A. In Vitro

Jurkat or Hut 78 cells obtained from ATCC and cultured in RPMI-1640 supplemented with 10% FCS, L-glutamine, non essential amino acids and 0.05 mM 2-mercaptoethanol, are centrifuged, washed once in PBS, and resuspended at $0.5 \times 10^6$ cells/ml in binding buffer (1.5% BSA, 5 mM glucose, 2 mM $MgCl_2$, 2ml $MnCl_2$ in TBS, pH 7) containing 5 μg/ml BCECF-AM (Molecular Probes). The cells are incubated at 37° C. for 30–45 min. in the dark. Then the cells are centrifuged and resuspended in binding buffer by pipetting and immediately used for experiment.

Flat well microtiter plates (NUNC Maxisorp) are coated with 1 μg/ml goat anti-mouse $C_K$ (Bioreba, South.Biot.) in carbonate buffer (15 mM $Na_2CO_3$, 35 mM $NaHCO_3$, pH8.0) 2 hours at 37° C. The plates are emptied and blocked with 1.5% BSA and 0.5% Tween-20 in carbonate buffer for 90 min. at 37° C. The plates are emptied and washed once in TBS containing, 1.5% BSA. Baculovirus derived ICAM-1 mouse $C_K$ fusion protein (100 ng/ml in TBS/1.5% BSA) is added to the wells. The plates are incubated for 90 min. at 37° C. After three washes with TBS/1.5% BSA, the compound to be tested is diluted in binding buffer (as above but free from BSA and glucose) and added to the wells. Then 100 000 Jurkat or Hut 78 cells/well are added and allowed to adhere for 30 min. at 37° C. Adherent cells are separated from non-adherent cells by 2–4 washes using binding buffer. Adherent cells are quantified with a fluorescence ELISA reader CytofluorII with the filters set at 485 nm and 530 nm emission.

In this assay, compounds of the invention inhibit adhesion of the Jurkat or Hut 78 cells to ICAM-1 with an $IC_{50} \leq 30$ μM, preferably 0.05 to 30 μM.

B. In Vivo i) Murine Thioglycollate Induced Peritonitis

Thioglycollate is injected i.p. to mice and immediately thereafter the compound to be tested is given s.c. The mice are killed after 4 hours, the peritoneal cavity lavaged and the total number of neutrophils in the lavage fluid is determined.

In this assay, the compounds of the invention, e.g. mevinolins inhibit thioglycollate induced neutrophil migration when administered s.c. at a dose of from 0.001–50 mg/kg.

ii) Ischemia/Reperfusion Injury

The compounds may be tested in a model of heart ischemia/reperfusion injury (Abdeslam Oubenaissa et al., Circulation, 94, Suppl. II, 254–258, 1996) or as follows:

Mice weighing 20–25 g are anaesthetized with isoflurane and the right renal vessels are clamped using microvascular clamps for 60 min. After 60 min of ischemia, the microvascular clamps are removed. The left renal vessels (renal artery, vein and ureter) are ligated using a 4-0surgical suture. The left (nonischemic) kidney is removed, and the abdominal cavity closed with 3-0 surgical suture. Sham groups undergo the same procedures as the ischemia group, but without clamping of the reight renal vessels.

Animals are sacrified by $CO_2$ inhalation at 24 h, 1 week and 2 weeks following reperfusion. Blood samples are collected by cardiac puncture into a 3.0 ml Vacutainer® tube (Becton-Dickensen) containing 0.04 ml of a 7.5% solutio of $K_3$ EDTA immediately after sacrifice. Plasma is separated and stored at $-20°$ C. until further analysis. Plasma creatinine and blood urea nitrogen (BUN) are analysed using Sigma procedures. Following sacrifice, the kidney is flushed with physiological saline, immediately snap-frozen in liquid nitrogen and stored at $-70°$ C. until analysis. Myeloperoxidase activity (MPO) in the kydney is measured according to the method of Bradley et al (J. Invest. Dermatol., 78, 206–209, 1982).

In this model, the compounds of the invention, e.g. the mevinolins reduce plasma creatinine and blood urea nitrogen when administered at a dose of 0.001 to 50 mg/kg, particularly for 4 days prior to ischemia.

iii) Vascularized Heterotopic Heart Transplantation

Mice donor hearts are implanted onto the recipients abdominal vessels: brachiocephalic trunk to aorta and right pulmonary artery to inferior vena cava with end-to-side anastomoses using 11/0 Ethilon (Ethicon, Norderstedt, Germany) continuous sutures. Animals are closed in two layers with 6/0 Vicryl (Ethicon) and kept warm until fully recovered. Total ischaemia times are in the range of 40–50 min of which 25–35 min are at 4° C. During anastomosis (10–15 min) the graft is kept cold.

After transplantation, graft function is monitored by daily assessment of graft beat (palpation). Rejection is considered to be complete when heart beat stops. In all experiments rejection is confirmed by histological examination of the grafts. Significant improvements of graft function are obtained in animals treated with a compound of the invention, e.g. a mevinolin, administered at daily a dose $\leq 50$ mg/kg.

The compounds of the invention, e.g. the mevinolins of the invention are, therefore, useful in the treatment and/or prevention of diseases or disorders mediated by LFA-1/ICAM-1 interactions e.g. ischemia/reperfusion injury e.g. myocardial infarction, stroke, gut ischemia, renal failure or hemorrhage shock, acute or chronic rejection of organ or tissue allo- or xenografts, acute or chronic inflammatory or autoimmune diseases, e.g. rheumatoid arthritis, asthma, allergy conditions, dermatological diseases, e.g. psoriasis, contact dermatitis, adult respiratory distress syndrome, inflammatory bowel disease and ophthalmic inflammatory diseases, infection diseases such as septic shock, traumatic shock.

For the above uses the required dosage will of course vary depending on the mode of administration, the particular condition to be treated and the effect desired. In general, however, satisfactory results are achieved at dosage rates of from about 0.5 to 80 mg/kg animal body weight. Suitable daily dosage rates for larger mammals, for example humans, are of the order of from about 20 mg to 1.5 g/day, e.g. 100 mg to 1,5 g/day conveniently administered once, in divided dosages 2 to 4×/day, or in sustained release form. Unit dosage forms suitably comprise from about 5 mg to 0.750 g of a compound of the invention, together with a pharmaceutical acceptable diluent or carrier therefor.

The mevinolins of the invention may be administered in free form or in pharmaceutically acceptable salt form e.g. acid addition salts or alkali salts such as sodium or potassium, or substituted or unsubstituted ammonium salts. Such salts may be prepared in conventional manner and exhibit the same order of activity as the free compounds.

In accordance with the foregoing the present invention further provides:

3. A method for preventing or treating disorders or diseases mediated by LFA-1/ICAM-1 interactions, e.g. such as indicated above in a subject in need of such treatment, which method comprises administering to said subject an effective amount of a compound of the invention, e.g. a mevinolin of the invention or a pharmaceutically acceptable salt thereof;

4. A pharmaceutical composition for use in the method as in 3) above comprising a compound of the invention, e.g. a mevinolin in free form or pharmaceutically acceptable salt form in association with a pharmaceutically acceptable diluent or carrier therefor.

5. A compound of the invention, e.g. a mevinolin or a pharmaceutically acceptable salt thereof for use in the preparation of a pharmaceutical composition for use in the method as in 3) above.

The pharmaceutical compositions may be manufactured in conventional manner.

The compounds of the invention, e.g. the mevinolins of the invention may be administered by any conventional route, for example enterally, preferably orally, e.g. in the form of tablets or capsules or parenterally e.g. in form of injectable solutions or suspensions, or in a nasal or a suppository form.

The mevinolins of the invention may be administered as the sole active ingredient or together with other drugs in immunomodulating regimens or other anti-inflammatory agents for the treatment or prevention of allo- or xenograft acute or chronic rejection or inflammatory or autoimmune disorders. For example, they may be used in combination with cyclosporins, rapamycins or ascomycins, or their immunosuppressive analogs, e.g. cyclosporin A, cyclosporin G, FK-506, rapamycin, 40-O-(2-hydroxy)ethyl-rapamycin etc.; corticosteroids; cyclophosphamide; azathioprene; methotrexate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; or other immunomodulatory compounds, e.g. CTLA4Ig, or other adhesion molecule inhibitors, e.g. mAbs or low molecular weight inhibitors including Selectin antagonists and VLA-4 antagonists.

Where the mevinolins of the invention are administered in conjunction with other immunosuppressive/immunomodulatory or anti-inflammatory therapy, e.g. for preventing or treating chronic rejection as hereinabove specified, dosages of the co-administered immunosuppressant, immunomodulatory or anti-inflammatory compound will of course vary depending on the type of co-drug employed, e.g. whether it is a steroid or a cyclosporin, on the specific drug employed, on the condition being treated and so forth. In accordance with the foregoing the present invention provides in a yet further aspect:

6. A method as defined above comprising co-administration, e.g. concomitantly or in sequence, of a therapeutically effective amount of a mevinolin of the invention in free form or in pharmaceutically acceptable salt form, and a second drug substance, said second drug substance being an immunosuppressant, immunomodulatory or anti-inflammatory drug, e.g. as indicated above.

7. A kit or package for use in any method as defined under 3) above, comprising a mevinolin of the invention, in free form or in pharmaceutically acceptable salt form, with at least one pharmaceutical composition comprising an immunosuppressant, immunomodulatory or anti-inflammatory drug. The kit or package may comprise instructions for its administration.

Representative mevinolins for use in accordance with the invention are those comprising a moiety of formula A

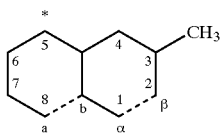

A which is further substituted in positions 4 and 5 and optionally in positions 6 or 7, each of a-b and α-β, independently being a single or double bond. Each of a-b and α-β may also be part of a cyclopropyl group. The moiety of formula A may be substituted in positions 4, 5, 6 and/or 7 with one or more substituents as described in literature for known mevinolins, e.g. as disclosed by Y. Chapleur (see above). Preferably the substituent in position 4 is a substituted methyl group. Preferably the substituent in position 5 is linked via —*O—CO— to the bicyclic residue; more preferably it is —*O—CO—$R_2$ wherein $R_2$ is $C_1$–$C_8$ alkyl, $C_{3-7}$ cycloalkyl, aryl, heteroaryl, $C_{3-7}$ cycloalkyl-$C_{1-4}$ alkyl, aryl-$C_{1-4}$ alkyl or heteroaryl-$C_{1-4}$ alkyl.

Preferred mevinolins of the invention for use as LFA-1 antagonist are compounds of formula I

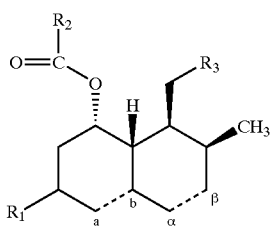

I wherein $R_2$ is as defined above, $R_1$ is ·····ııııH, ·····ııııı$C_{1-4}$alkyl or ━━━$OR_a$;

$R_a$ is H; $C_{1-6}$ alkyl; $C_{1-6}$ alkyl substituted by OH or $C_{1-4}$ alkoxy; $C_{2-6}$ alkenyl; or aryl-$C_{1-4}$ alkyl;

$R_3$ is a radical of formula (i), (ii), (iii) or (iv)

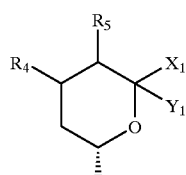

(i)

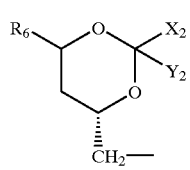

(ii)

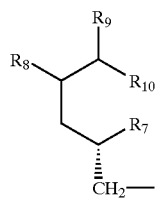

(iii)

or

(iv)

wherein $X_1$ and $Y_1$ are (H,H), (H,OH) or =O;

$X_2$ and $Y_2$ are =O or (R,R) wherein each R independently is H, $C_{1-3}$ alkyl, substituted $C_{1-3}$ alkyl or $X_2$ and $Y_2$ form together with the cabon atom to which they are bound a 4-, 5-, 6- or 7- membered carbo- or heterocyclic residue, $R_4$ is $OR_a$ wherein $R_a$ is as defined above; or —O—$COR_b$ wherein $R_b$ is $C_{1-8}$ alkyl optionally substituted by OH, $C_{3-7}$ cycloalkyl, $C_{3-7}$ cycloalkyl-$C_{1-4}$ alkyl, aryl, aryl-$C_{1-4}$ alkyl, heteroaryl or heteroaryl-$C_{1-4}$ alkyl; or $NR_cR_d$ wherein each of $R_c$ and $R_d$, independently, is $C_{1-6}$alkyl or form together with the nitrogen to which they are bound a heterocyclic radical optionally comprising an oxygen or another nitrogen atom;

$R_5$ is H, $C_{1-4}$ alkyl, $C_{3-9}$ alkenyl, $C_{3-9}$ alkynyl, aryl-$C_{1-4}$ alkyl, or $C_{3-7}$ cycloalkyl-$C_{1-4}$ alkyl;

$R_6$ is —$CHR_{11}$—CO—$NR_{12}R_{13}$ wherein $R_{11}$ has one of the significances as given for $R_5$ and each $R_{12}$ and $R_{13}$, independently, is H, $C_{1-4}$ alkyl, or substituted $C_{1-4}$ alkyl;

$R_7$ is =O or (H,OH);

$R_8$ is $OR_a$; or $NR_eR_f$ wherein each of $R_e$ and $R_f$, independently, is H, $C_{1-6}$alkyl, $C_{1-6}$alkyl substituted by OH or $C_{1-4}$alkoxy, or a 5-membered heterocyclic residue;

or $R_7$ and $R_8$ together form a dioxy-$C_{1-4}$alkylene group or —O—CO—O—;

$R_9$ has one of the significances given for $R_5$;

$R_{10}$ is $COOR_a$; $CH_2OR_c$ wherein $R_c$ is $R_a$ or $COR_b$; or $CONR_{14}R_{15}$ or $CH_2NR_{14}R_{15}$ wherein each of $R_{14}$ and $R_{15}$ independently is $C_{1-4}$alkyl, hydroxy substituted $C_{1-4}$alkyl, carbamoyl-methyl, ($C_{1-4}$alkyl)-carbamoyl-methyl or di($C_{1-4}$alkyl)-carbamoyl-methyl, or one of $R_{14}$ and $R_{15}$ is hydrogen and the other is $C_{1-6}$alkyl, $C_{1-6}$alkyl substituted by OH and/or a group selected from carbamoyl, ($C_{1-4}$alkyl)-carbamoyl, di($C_{1-4}$alkyl)-carbamoyl and heteroaryl-$C_{1-4}$alkyl, $C_{1-6}$alkoxy-carbonyl-methyl, adamantyl-methyl, $C_{3-7}$cycloalkyl-$C_{1-4}$alkyl, aryl-$C_{1-4}$alkyl wherein aryl may be substituted and $C_{1-4}$alkyl may be substituted by carbamoyl or $C_{1-4}$alkoxy-carbonyl, or heteroaryl-$C_{1-4}$alkyl wherein heteroaryl may be substituted by carbamoyl or $C_{1-4}$alkoxy-carbonyl and $C_{1-4}$alkyl may be substituted by carbamoyl, or $R_{14}$ and $R_{15}$ form together with the nitrogen to which they are attached a heterocyclic residue optionally comprising a further nitrogen atom and optionally substituted by $C_{1-4}$alkyl, ($C_{1-4}$alkoxy)-carbonyl, carbamoyl, dioxy-$C_{1-4}$alkylene, aryl-$C_{1-4}$alkyl or heteroaryl wherein heteroaryl may be substituted by $C_{1-4}$alkoxy-carbonyl;

$R_{16}$ is H; $C_{1-4}$alkyl; aryl-$C_{1-4}$alkyl wherein aryl may be substituted by halogen, OH, amino optionally substituted, COOH, CF$_3$, $C_{1-4}$ alkoxy or cyano; or $C_{3-7}$cycloalkyl-$C_{1-4}$aryl;

each of a-b and α-β independently, is either a single bond or a double bond, in free form or in a pharmaceutically acceptable salt form.

Alkyl groups as $R_a$ $R_b$, $R_2$, $R_5$, $R_{11}$, $R_{12}$ or $R_{13}$ or alkyl moieties may be branched or straight chain. When R, $R_{12}$ or $R_{13}$ is a substituted alkyl, the substituent is preferably located at the end of the alkyl chain and may be e.g. halogen, OH, $C_{3-7}$ cycloalkyl or aryl. When $R_e$ or $R_f$ is substituted $C_{1-6}$alkyl, it is preferably substituted at the end of the alkyl chain.

Cycloalkyl groups or moieties are preferably cyclopentyl or cyclohexyl.

Aryl or aryl moiety is preferably phenyl and may be substituted, e.g. by halogen, OH, amino optionally substituted, COOH, CF$_3$, $C_{1-4}$ alkoxy or cyano, preferably by 1,2 or 3 $C_{1-4}$alkoxy. Aryl-$C_{1-4}$ alkyl is preferably phenyl-$C_{1-4}$ alkyl, e.g. benzyl or phenethyl.

Heteroaryl is preferably derived from a 5- or 6-membered heterocycle optionally fused to a benzene ring, e.g. pyrrolyl, imidazolyl, furyl, thienyl, pyridyl, indolyl etc. When $R_c$ and $R_d$ form together with the nitrogen to which they are attached a heterocyclic radical, this may be a 5- or 6-membered ring, e.g. pyrrolidinyl, piperidyl, piperazinyl, 4-methyl-piperazinyl. When one of $R_{14}$ or $R_{15}$ is heteroaryl-$C_{1-4}$alkyl, the heteroaryl moiety may be a 5- or 6-membered, optionally fused to a benzene ring or a heterocyclic residue, e.g. furyl, morpholino, piperazinyl or indolyl. When $R_{14}$ and $R_{15}$ form together with the nitrogen to which they are attached a heterocyclic residue, this may be e.g. pyrrolidinyl, piperidino, piperazinyl.

When $X_2$ and $Y_2$ form a carbo- or heterocyclic residue, it may be e.g. cyclopropyl, cyclobutyl, cyclopentyl, cyclohexyl, cyclohexenyl, pyrrolidinyl, pyrrolidonyl.

The alkylene moiety in dioxy-$C_{1-4}$alkylene may be linear, e.g. —CH$_2$—, —CH$_2$—CH$_2$—, or branched, e.g. =C(CH$_3$)$_2$.

Compounds of formula I may exist in free form or in salt form, e.g. acid addition salts with e.g. organic or inorganic acids, for example, hydrochlorides, or salt forms obtainable when a COOH is present, as salts with bases e.g. alkali salts such as sodium or potassium, or substituted or unsubstituted ammonium salts.

It will be appreciated that in the residues of formulae (i), (ii) and (iii) the carbon atoms bearing $R_4$, $R_5$, $R_6$, $R_7$, and $R_8$ may be asymetric. Where in the molecule of formula I the stereochemistry is not indicated, it is to be understood that the present invention embraces all enantiomers and their mixtures. Similar considerations apply in relation to starting materials exhibiting asymetric carbon atoms as mentioned above.

In the compounds of formula I, the following significances are preferred:

1. $R_1$ is H or CH$_3$, preferably CH$_3$;
2. $R_2$ is $C_{4-8}$alkyl, preferably —CH(CH$_3$)—CH$_2$—CH$_3$; —CH(CH$_2$—CH$_2$—CH$_3$)$_2$—; —CH(CH$_2$CH$_3$)$_2$;

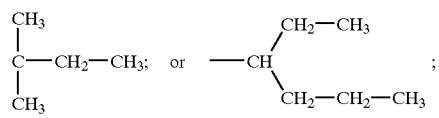

3. $R_3$ is a radical of formula (i);
4. $R_3$ is a radical of formula (iii);
5. $R_3$ is a radical of formula (iii) wherein $R_7$ is (H,OH);
6. $R_3$ is a radical of formula (iii) wherein $R_7$ is =O;
7. $R_3$ is a radical of formula (iii) wherein $R_8$ is OH;
8. $R_3$ is a radical of formula (iii) wherein $R_7$ and $R_8$ form together a dioxy-$C_{1-4}$alkylene group or —O—CO—O—;
9. $R_3$ is a radical of formula (iii) wherein $R_8$ is $NR_eR_f$;
10. $R_3$ is a radical of formula (iii) wherein $R_8$ is $NHR_f$ wherein $R_f$ is $C_{1-6}$alkyl optionally substituted by OH or $C_{1-4}$alkoxy;
11. $R_3$ is a radical of formula (iii) wherein $R_9$ is H, CH$_3$, benzyl or propargyl;
12. $R_3$ is a radical of formula (iii) wherein $R_{10}$ is CONR$_{14}$R$_{15}$;
13. $R_3$ is a radical of formula (iii) wherein $R_{10}$ is CONHR$_{15}$ wherein $R_{15}$ is $C_{1-4}$alkyl optionally substituted by OH;
14. $R_3$ is a radical of formula (iii) wherein $R_{10}$ is CONHR$_{15}$ wherein $R_{15}$ is phenyl-$C_{1-4}$alkyl or heteroaryl-$C_{1-4}$alkyl wherein the phenyl, heteroaryl and $C_{1-4}$alkyl moieties may be substituted as indicated above. Preferably phenyl is substituted by 1, 2 or 3 $C_{1-4}$alkoxy, particularly OCH$_3$;
15. $R_{15}$ is CH$_2$-phenyl or CH(CO—OCH$_3$)-phenyl wherein phenyl may be substituted by 1,2 or 3 $C_{1-4}$alkoxy, preferably OCH$_3$;
16. $R_{15}$ is CH$_2$-furyl or CH(CONH$_2$)—CH$_2$-3-indolyl;
17. $R_{10}$ is —CONR$_{14}$R$_{15}$ wherein $R_{14}$ and $R_{15}$ form together with the nitrogen to which they are attached an optionally substituted piperidinyl group, e.g. substituted by dioxy-$C_{1-4}$alkylene, preferably dioxy-ethylene;
18. $R_3$ is a radical of formula (iv).

Among the mevinolins of formula I, the compounds of formula II

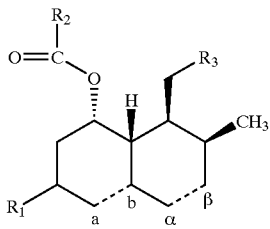

wherein $R_1$, $R_2$, $R_3$ and the doted lines a-b and α-β are as defined above, provided that 1) $R_2$ is other than $C_{1-5}$ alkyl or aryl-$C_{1-4}$ alkyl when $R_1$ is H, $CH_3$ or $C_2H_5$ and $R_3$ is a radical of formula (i) wherein $R_4$ is OH or $OCH_3$, $R_5$ is H or $C_{1-4}$ alkyl, and $X_1$ and $Y_1$ are =O, or
2) $R_2$ is other than $C_{1-5}$ alkyl when $R_3$ is a radical of formula (iii) wherein $R_9$ is H and $R_{10}$ is $COOR_a$, or salt thereof, are novel and form part of the present invention.

Particularly preferred compounds of formula II are those wherein

1. $R_1$ is H or $CH_3$, preferably $CH_3$
2. $R_2$ is $C_{4-8}$alkyl, preferably as disclosed above;
3. $R_3$ is a radical of formula (iii);
4. $R_3$ is a radical of formula (iii) wherein $R_8$ is $NHR_f$ wherein $R_f$ is $C_{1-6}$alkyl optionally substituted by OH or $C_{1-4}$alkoxy;
5. $R_3$ is a radical of formula (ii) wherein $R_{10}$ is $CONHR_{15}$ wherein $R_{15}$ is $C_{1-4}$alkyl optionally substituted by OH, preferably OH substituted $C_{1-4}$alkyl;
6. $R_3$ is a radical of formula (iii) wherein $R_{10}$ is $CONHR_{15}$ wherein $R_{15}$ is phenyl-$C_{1-4}$alkyl wherein the phenyl moiety may be substituted by 1, 2 or 3 $C_{1-4}$alkoxy, preferably $OCH_3$.

The present invention also includes a process for the production of the compounds of formula II, comprising
a) for the production of a compound of formula II wherein $R_3$ is a radical of formula (i) or (ii) reacting a compound of formula III

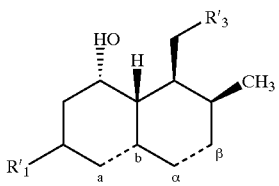

wherein a-b and α-β are as defined above, $R'_1$, has one of the significances given for $R_1$ except that the OH group as $R_1$ has to be in protected form and $R'_3$ is a radical of formula (i) or (ii)

with a compound of formula IV

 COOH    IV wherein $R_2$ is as defined above, or a functional derivative thereof, or b) converting mevinolin or compactin into a compound of formula I;

and, where required, removing the protecting group, and recovering the compounds of formula II thus obtained in free form or in salt form.

Where OH groups are present in the starting products which are not to participate in the reaction, they may be protected, in accordance with known methods. OH protecting groups are known in the art, e.g. t.-butyl-dimethyl-silanyl.

Process step a) may be performed in accordance with known esterification methods. A functional derivative of a compound of formula IV includes e.g. an acid halogenide, ester or anhydride.

Process step b) may be a substitution in position 5 or a reduction of the pyranyl residue, e.g. as disclosed in Example 3. The $R_2$—CO—O— group of mevinolin may also be reduced to OH and then esterified to another $R_2$—CO—O— group. To produce compounds of formula II wherein $R_3$ is a residue of formula (iii) where $R_{10}$ is $CONR_{14}R_{15}$, a compound of formula II wherein $R_3$ is a radical of formula (i) or (ii) e.g. mevinolin or compactin, may be submitted to ring opening, e.g. by reaction with a corresponding amine, e.g. alkylamine, HO-alkyl-amine, heterocyclic amine, or via the azide route. When $R_7$ is (H,OH), it may be oxidized to =O in accordance with known oxidation methods, e.g. with sulfur trioxide in form of a pyridine complex or according to a Swern oxidation. The preparation of compounds of formula II wherein $R_7$ and $R_8$ in the radical of formula (iii) form together a carbonate or dioxy-alkylene group, may be performed according to known methods, e.g. using preferably carbonyldiimidazole for the carbonate, or via ketal formation for the dioxy-alkylene group.

Process step b) may also be a cyclisation of a compound of formula II wherein $R_3$ is a radical of formula (iii) to produce a compound of formula II wherein $R_3$ is a radical of formula (i) or (iv). The cyclisation may advantageously be performed in the presence of a base e.g. Hunig's base and an activating agent, e.g. trifluoromethane sulfonic anhydride. The preparation of a compound of formula II wherein $R_3$ is a radical of formula (iv) may conveniently be performed using a compound of formula II wherein $R_3$ is a radical of formula (iii) wherein $R_{10}$ is $CONHR_{15}$ and $R_7$ is oxidized to =O. Cyclisation may be carried out by acidic treatment, e.g. using trifluoroacetic acid.

Insofar as the production of the starting materials is not particularly described, the compounds are known or may be prepared analogously to methods known in the art, as disclosed by Y. Chapleur, in "Progress in the Chemical Synthesis of Antibiotics and Related Microbial Products", Springer Verlag, 1993, vol. 2, 829–93.

The present invention further provides:

8. A compound of formula II or a pharmaceutically acceptable salt thereof for use as a pharmaceutical, e.g. in the treatment or prevention of disorders or diseases as indicated above.
9. A pharmaceutical composition comprising a compound of formula II, or a pharmaceutically acceptable salt thereof in association with a pharmaceutically acceptable diluent or carrier therefor.

The following examples are illustrative of the invention.

EXAMPLE 1

2-Ethyl-butyric Acid 8-[2-(4-Hydroxy-6-oxo-tetrahydro-pyran-2-yl)-ethyl]-3,7-dimethyl-1,2,3,7,8, 8a-hexahydro-naphthalen-1-yl Ester To a solution of 152 mg (0.350 mmol) of 4-(tert-butyl-dimethyl-silanyloxy)-6-[2-(8-hydroxy-2,6-dimethyl-1,2,6, 7,8,8a-hexahydro-naphthalen-1-yl)-ethyl]-tetrahydro-pyran-2-one in 2 ml of pyridine are added 927 mg (4.39 mmol) of 2-ethyl-butyric acid anhydride and the mixture is stirred overnight at room temperature. The reaction is quenched with saturated aqueous sodium bicarbonate. The aqueous phase is separated and extracted twice with methyl-t-butyl ether. The organic phases are combined, washed with a 10% citric acid solution and dried over sodium sulfate. The crude product is dissolved in 5 ml of THF containing 75 mg (1.3 mmol) acetic acid and 0.3 g (1 mmol) of tetrabutyl ammonium fluoride trihydrate are added. After 20 hours at room temperature the reaction is quenched with saturated aqueous sodium bicarbonate. The phases are separated and the water phase is extracted twice with ethyl acetate. The organic phases are combined, washed with brine and dried over sodium sulfate. After evaporation of the solvent, the crude product is purified by silica gel chromatography (methyl-t-butyl ether) to afford the desired product which is recrystallized from diethyl ether/hexane.

m.p. 120–122° C. (diethyl ether/hexane); MS (ESI) 441 (M+Na), 419 (M+H).

EXAMPLE 2

2-Methyl-butyric Acid 8-[2-(5-Benzyl-4-hydroxy-6-oxo-tetrahydro-pyran-2-yl)-ethyl]-3,7-dimethyl-1,2,3,7,8,8a-hexahydro-naphthalen-1-yl Ester To a stirred, cooled (−77° C.) solution of 101 mg (1.00 mmol) of diisopropylamine in 5 ml of THF under argon are added 0.63 ml (1.0 mmol) of a 1.6 M butyllithium solution in hexane.

After 15 minutes, 202 mg (0.50 mmol) of mevinolin are added and the reaction mixture is kept at −77° C. for 30 minutes. Then 171 mg (1.0 mmol) benzyl bromide are added. After 2 hours the reaction is let come to room temperature and poured onto 0.1 N aqueous HCl. The phases are separated and the aqueous phase is extracted twice with ethyl acetate. The organic phases are combined, washed with brine and dried over sodium sulfate. The solvent is evaporated and the crude product is purified by silica gel chromatography (diethyl ether/hexane 2/1) to afford the desired product as a colorless oil.

MS (FAB) 495 (M+H), 393.

EXAMPLE 3

2-Methyl-butyric Acid 8-[2-(4-Hydroxy-tetrahydro-pyran-2-yl)-ethyl]-3,7-dimethyl-1,2,3,7,8,8a-hexahydro-naphthalen-1-yl Ester To a solution of 65 mg (0.15 mmol) of mevinolin in 5 ml of ethanol are added 22 mg (1.0 mmol) lithium borohydride and the resulting mixture is stirred overnight at room temperature. The reaction is quenched with 0.1 N aqueous HCl. The phases are separated and the aqueous phase is extracted twice with ethyl acetate. The organic phases are combined, washed with brine and dried over sodium sulfate. The solvent is evaporated and the crude product purified by silica gel chromatography (ethyl acetate) to afford 2-methyl-butyric acid 3,7-dimethyl-8-(3,5,7-trihydroxy-heptyl)-1,2,3,7,8,8a-hexahydro-naphthalen-1-yl ester as an oil.

MS (ESI) 431 (M+Na), 409 (M+H).

To a cooled (−77° C.) solution of 73 mg (0.18 mmol) of 2-methyl-butyric acid 3,7-dimethyl-8-(3,5,7-trihydroxy-heptyl)-1,2,3,7,8,8a-hexahydro-naphthalen-1-yl ester in 5 ml of methylene chloride is added 0.9 g (7 mmol) Hunig's base and 0.08 ml (0.5 mmol) triflic anhydride. After 30 minutes the reaction is quenched with saturated aqueous sodium bicarbonate. The phases are separated and the water phase is extracted twice with ethyl acetate. The organic phases are combined, washed with brine and dried over sodium sulfate. The solvent is evaporated and the crude product is purified by silica gel chromatography (diethyl ether/hexane 1/4) to afford the desired product as a colorless oil.

MS (FAB) 391 (M+H), 289.

EXAMPLE 4

2-Methyl-butyric Acid 8-(6-Benzylcarbamoyl-3,5-dihydroxy-hexyl)-3,7-dimethyl-1,2,3,7,8,8a-hexahydro-naphthlen-1-yl Ester To a solution of 0.13 g (0.32 mmol) of mevinolin in 15 ml of THF are added 0.5 ml (5 mmol) benzylamine. The stirred reaction mixture is heated at reflux for 7 hours. After cooling to room temperature the reaction is diluted with 20 ml of methyl-t-butyl ether and washed successively with 0.1 N HCl and brine. The organic phase is then dried over sodium sulfate and the solvent evaporated. The crude product is purified by silica gel chromatography (ethyl acetate) to afford the desired product as an oil.

MS (ESI) 534 (M+Na), 512 (M+H).

EXAMPLE 5

Preparation of the Compound 33 in Table 3

A solution of 200 mg Mevinolin in 5 ml THF and 1.0 ml Hydrazine-Hydrat (25% in $H_2O$) is stirred at room temperature for 15 hours. After concentration, the reaction mixture is diluted with EtOAc, washed with water and brine, dried ($Na_2SO_4$), and concentrated. 2-Methyl-butyric acid 8-(6-hydrazinocarbonyl-3,5-dihydroxy-hexyl)-3,7-dimethyl-1,2,3,7,8,8a-hexahydro-naphthalen-1-yl ester cristallizes from $Et_2O$.

To a stirred, cooled solution (−15° C.) of 86 mg of the above hydrazide are successively added 1.0 ml of 5N HCl in $Et_2O$ and 0.36 ml of a 10% solution of tert.-butylnitrite in DMF. After 15 minutes stirring at −15° C., 0.15 ml $NEt_3$ and 0.06 ml 1,4-dioxa-8-azaspiro[4,5]decane are added. The reaction mixture is stirred 15 hours at 0° C. then concentrated under reduced pressure, diluted with EtOAc, washed with 0.1N HCl, brine, sodium bicarbonate, brine, dried ($Na_2SO_4$) and concentrated. The product of Example 33 is obtained after cristallization with diisopropylether.

MS (ESI): 548 $MH^+$.

EXAMPLE 6

2-Methyl-butyric Acid 8-[3-Hydroxy-5-(2-hydroxy-ethylamino)-6-(2-hydroxy-ethylcarbamoyl)-hexyl]-3,7-dimethyl-1,2,3,7,8,8a-hexahydro-naphthalen-1-yl Ester To a stirred solution of 4.0 g (10 mmol) mevinolin in 20 ml pyridine at room temperature are added 20 ml acetic acid anhydride. After 1 h the reaction mixture is concentrated in-vacuo. The residue is dissolved with 10 ml methyl-t-butyl ether and washed successively with water, 0.1 N HCl and brine. The organic phase is then dried over sodium sulfate and the solvent removed in vacuo. The crude product is purified by silica gel chromatography (methyl-t-butyl ether 1/3) to afford 2-methyl-butyric acid 3,7-dimethyl-8-[2-(6-oxo-3,6-dihydro-2H-pyran-2-yl)-ethyl]-1,2,3,7,8,8a-hexahydro-naphthalen-1-yl ester) as a white powder.

To a stirred solution of 1.2 g (3.0 mmol) (methyl-t-butyl ether 1/3) to afford 2-methyl-butyric acid 3,7-dimethyl-8-[2-(6-oxo-3,6-dihydro-2H-pyran-2-yl)-ethyl]-1,2,3,7,8,8a-hexahydro-naphthalen-1-yl ester) in 10 ml THF at room temperature are added 1.5 ml (25 mmol) ethanol amine. After 12 h the solvent is evaporated and the residue dissolved in 10 ml ethyl acetate. The solution is washed with 5 ml saturated aqueous sodium bicarbonate and 5 ml brine. The solution is then dried over sodium sulfate and the solvent evaporated to afford the title product as a hygroscopic foam.

MS (ESI) 515 (M+Li), 509 (M+H).

By following the procedures as disclosed above in the Examples, but using the appropriate starting materials, the compounds of formula $X_1$

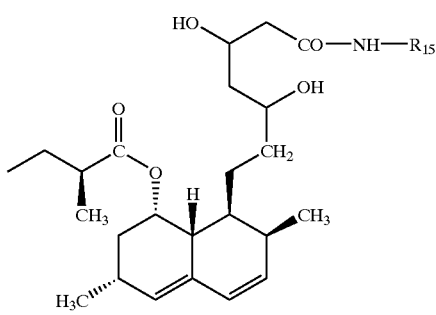

wherein $R_{15}$ is as defined in Table 1 below, may be prepared.

TABLE 1

| Ex | $R_{15}$ | | MS | |
|---|---|---|---|---|
| 7 | CH$_2$-phenyl-OCH$_3$ | ESI | 542 | MH$^+$ |
| 8 | CH$_2$-3-indolyl / CH / CONH$_2$ | ESI | 606 | MH$^-$ |
| 9 | isobutyl | FAB | 478 | MH$^+$ |
| 10 | CH$_2$—CO—O-t.butyl | FAB | 536 | MH$^+$ |
| 11 | CH$_2$-cyclohexyl | FAB | 518 | MH$^+$ |
| 12 | CH$_2$-phenyl(OCH$_3$)(OCH$_3$) | FAB | 572 | MH$^+$ |
| 13 | C(CH$_2$—OH)$_3$ | ESI | 524 | MH$^-$ |
| 14 | CH$_2$—CH$_2$-morpholino | ESI | 535 | MH$^+$ |
| 15 | CH$_2$-phenyl-OCH$_3$ | ESI | 542 | MH$^+$ |

TABLE 1-continued

| Ex | $R_{15}$ | | MS | |
|---|---|---|---|---|
| 16 | CH$_3$—CH(CH)(OH) / CONH$_2$ | ESI | 521 | MH$^-$ |
| 17 | CH$_2$-furyl | ESI | 502 | MH$^+$ |
| 18 | isobutyl-CH / CONH$_2$ | FAB | 535 | MH$^+$ |
| 19 | CH$_2$OH / CH / CONH$_2$ | ESI | 507 | MH$^-$ |
| 20 | CH$_2$—CO—N(CH$_3$)$_2$ | FAB | 507 | MH$^+$ |
| 21 | CH(phenyl) / COOCH$_3$ | ESI | 568 | MH$^-$ |
| 22 | CH(CH$_3$)—CONH$_2$ | ESI | 491 | MH$^-$ |

By following the procedures as disclosed above in the Examples, but using the appropriate starting materials, the compounds of formula $X_2$

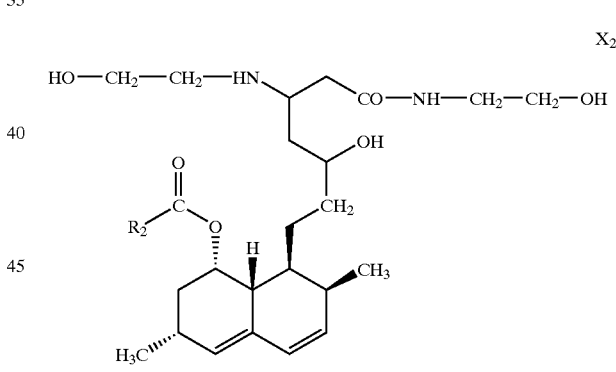

wherein $R_2$ is as defined in Table 2 below, may be prepared.

TABLE 2

| Ex | $R_2$ | | MS | |
|---|---|---|---|---|
| 23 | CH(CH$_2$—CH$_2$—CH$_3$)$_2$ | FAB | 557 | M + Li$^+$ |
| 24 | CH$_3$—C(CH$_3$)—CH$_2$—CH$_3$ | FAB | 529 | M + Li$^+$ |

By following the procedures as disclosed above and below, but using the appropriate starting materials, the compounds of formula $X_3$

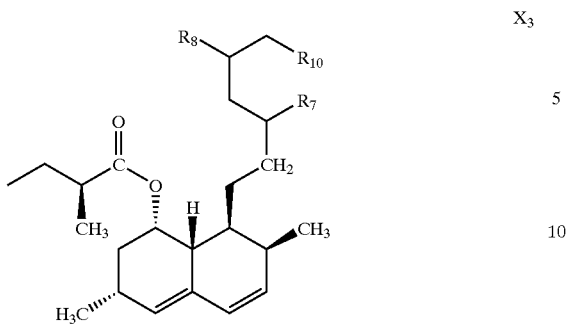

wherein $R_7$, $R_8$ and $R_9$ are as defined in Table 3 below, may be prepared.

TABLE 3

| Ex | $R_7$ | $R_8$ | $R_{10}$ | | MS | |
|---|---|---|---|---|---|---|
| 25 | OH | piperazinyl | CO—OC$_2$H$_5$ | FAB | 539 | M + Li$^+$ |
| 26 | OH | OH | CO—N(CH$_3$)$_2$ | FAB | 450 | MH$^+$ |
| 27 | OH | OH | CO—N(piperazine)—COOEt | ESI | 563 | MH$^+$ |
| 28 | OH | OH | CO—N(CH$_2$—CH$_3$)((CH$_2$)$_2$—OH) | ESI | 494 | MH$^+$ |
| 29 | OH | OH | CO—N(piperazine)—(indole-CO—OCH$_3$) | ESI | 562 | MH$^-$ |
| 30 | (CH$_3$)$_2$C(O—)(O—) | | CO—NH—CH$_2$-furan | ESI | 542 | MH$^+$ |
| 31 | OH | OH | CO—N[CH$_2$—CH(CH$_3$)(OH)]$_2$ | ESI | 538 | MH$^+$ |
| 32 | OH | OH | CO—N(CH$_3$)—CH$_2$—CO—N(CH$_3$)$_2$ | ESI | 521 | MH$^+$ |
| 33 | OH | OH | CO—N(piperidine-dioxolane spiro) | ESI | 548 | MH$^+$ |
| 34 | OH | OH | H$_2$N—CO-(pyrrolidine)-CO— | ESI | 519 | MH$^+$ |
| *35 | =O | OH | CO—NH—CH$_2$—C$_6$H$_4$—OCH$_3$ | ESI | 529 | M$^+$HCOO$^-$ |

TABLE 3-continued

| Ex | $R_7$ | $R_8$ | $R_{10}$ | | MS | |
|---|---|---|---|---|---|---|
| **36 | OH | OH | 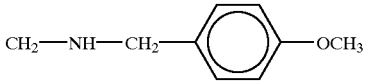 CH$_2$—NH—CH$_2$—C$_6$H$_4$—OCH$_3$ | ESI | 548 | MH$^+$ |
| ***37 | 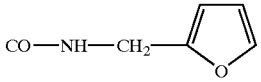 carbonate group | | CO—NH—CH$_2$-furyl | ESI | 528 | MH$^+$ |
| 38 | =O | OH | CO—NH—CH$_2$—C$_6$H$_5$ | FAB | 516 | M + Li$^+$ |
| 39 | =O | OH | CO—NHCH$_3$ | FAB | 440 | M + Li$^+$ |
| 40 | OH | OH | CO—N(piperazinyl)—CH$_2$—C$_6$H$_5$ 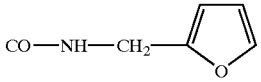 | FAB | 581 | MH$^+$ |
| 41 | OH | OH | CH$_2$—NH—CH$_2$-furyl 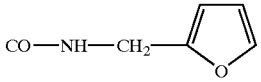 | ESI | 488 | MH$^+$ |
| 42 | OH | OH | CH$_2$—N(1,4-dioxa-8-azaspiro[4.5]decyl) 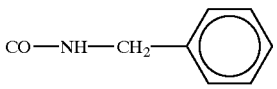 | ESI | 534 | MH$^+$ |
| 43 | OH | OH | CH$_2$—NH—CH(CONH$_2$)—CH$_2$-3-indolyl | ESI | 592 | MH$^-$ |
| 44 | OH | OH | CO—NH—CH$_2$—C$_6$H$_4$—OCH$_3$ 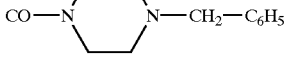 | ESI | 540 | MH$^-$ |

\* Oxidatation Example (Compound of Ex. 35)

A solution of 0.18 ml oxalyl chloride in 10 ml CH$_2$Cl$_2$ is slowly treated at −60° C. with 0.33 ml DMSO. After 15 minutes stirring at −60° C. a cold solution (−78° C.) of 2-methyl-butyric acid 8-[5-(tert-butyl-dimethyl-silanyloxy)-3-hydroxy-6-(4-methoxy-benzylcarbamoyl)-hexyl]-3,7-dimethyl-1,2,3,7,8,8a-hexahydro-naphthalen-1-yl ester in 5 ml CH$_2$Cl$_2$ is added. After 2 hours at −60° C., 0.80 ml of NEt$_3$ is added and the temperature is slowly rised to room temperature. After 2 hours at room temperature the reaction is quenched with H$_2$O. The phases are separated and the organic phase dried and concentrated. The crude product is purified by silica gel chromatography (CH$_2$Cl$_2$/MeOH). The resulting compound is dissolved in THF and treated with AcOH and Bu$_4$NF.3H$_2$O. After 30 hours the reaction mixture is concentrated, diluted with AcOEt and washed with H$_2$O, sat. NaHCO$_3$, brine, then dried (Na$_2$SO$_4$) and concentrated. The crude product is purified by silica gel chromatography. Pure fractions are combined and evaporated to afford 2-methyl-butyric acid 8-[5-hydroxy-6-(4-methoxy-benzylcarbamoyl)-3-oxo-hexyl]-3,7-dimethyl-1,2,3,7,8,8a-hexahydro-naphthalen-1-yl ester as foam.

\*\* Reduction Example (Compound of Ex. 36)

To a solution of 2.0 g 2-methyl-butyric acid 8-{2-[4-(tert-butyl-dimethyl-silanyloxy)-6-oxo-tetrahydropyran-2-yl]-ethyl}-3,7-dimethyl-1,2,3,7,8,8a-hexahydro-naphthalen-1-yl ester in 12 ml abs. THF under argon are slowly added under stirring at −78° C. 8.0 ml di-isobutyl aluminiumhydride (1 M) in THF. After 30 minutes stirring at −78° C., a mixture of 1.5 ml MeOH in 3 ml THF is slowly added. After 15 minutes, the reaction mixture is concentrated, diluted with EtOAc and washed with 10% citric acid, H$_2$O, sat. NaHCO$_3$, brine, dried (Na$_2$SO$_4$) and concentrated in vacuo. The lactol is obtained as a foam and stored at −20° C. 300 mg of the crude lactol in a mixture of 10 ml DMF and 1 ml AcOH under argon are treated with 74 mg NaCNBH$_3$ and 0.25 ml 4-methoxybenzylamine. After stirring at room temperature for 40 hours the reaction mixture is concentrated in vacuo, diluted with AcOEt and cold 1N HCl and stirred for 30 minutes. The organic phase is further washed with brine, sat. NaHCO$_3$, brine, dried and concentrated. The crude product is purified by silica gel chromatography (CH$_2$Cl$_2$/MeOH 95:5) to afford 2-methyl-butyric acid 8-[5-(tert-butyl-dimethyl-silanyloxy)-3-hydroxy-7-(4-methoxy-benzylamino)-heptyl]-3,7-dimethyl-1,2,3,7,8,8a-hexahydro-naphthalen-1-yl ester.

For deprotection the product is treated at room temperature with a mixture of 2 ml THF containing 20 μl AcOH and 77 mg tetrabutyl ammonium fluoride trihydrate. After stirring for 30 hours the reaction mixture is concentrated, diluted with AcOEt, washed with H$_2$O, sat. NaHCO$_3$, brine, dried (Na$_2$SO$_4$) and evaporated. 2-Methyl-butyric acid 8-[3,5-dihydroxy-7-(4-methoxy-benzylamino)-heptyl]-3,7-dimethyl- 1,2,3,7,8,8a-hexahydro-naphthalen-1-yl ester is obtained as a foam.

*** Conversion of Compound of Ex 17 into Compound of Ex 37

100 mg of compound of Ex 17 in 2 ml CH$_2$Cl$_2$ are treated with 73 mg DMAP, and 0.13 ml phosgen (2 M) in toluene. After stirring at room temperature overnight, the reaction mixture is quenched with sodium bicarbonate. The reaction mixture is then concentrated, diluted with Et$_2$O and successively washed with in HCl, H$_2$O, sat. NaHCO$_3$, brine, dried (Na$_2$SO$_4$) and concentrated. The desired product is cristallized from Et$_2$O/diisopropylether. (DMAP=dimethylaminopyridine).

EXAMPLE 45

2-Methyl-butyric Acid 8-[2-(1-Benzyl-6-oxo-1,6-dihydro-pyridin-2-yl)-ethyl]-3,7-dimethyl-1,2,3,7,8, 8a-hexahydro-naphthalen-1-yl Ester To a stirred solution of 2.6 g (5.0 mmol) 2-methyl-butyric acid 8-{2-[4-(tert.-butyl-dimethyl-silanyloxy)-6-oxo-tetrahydro-pyran-2-yl]-ethyl}-3,7-dimethyl-1,2,3,7,8,8a-hexahydro-naphthalen-1-yl ester in 50 ml toluene at room temperature are added 2.0 ml (18 mmol) benzylamine and 1 mg of Amberlite IP 120. The reaction mixture is heated at reflux for 18 hours. After cooling to room temperature the mixture is filtered, washed with 10% aqueous citric acid and dried over sodium sulfate. The solvent is evaporated to afford 2-methyl-butyric acid 8-[6-benzylcarbamoyl-5-(.tert.-butyl-dimethyl-silanyloxy)-3-hydroxy-hexyl]-3,7-dimethyl-1,2,3,7,8,8a-hexahydro-naphthalen-1-yl ester as an oil. MS (FAB) m/z 632 ([M+Li]$^+$).

To a stirred solution of 2.9 g (4.6 mmol) 2-methyl-butyric acid 8-[6-benzylcarbamoyl-5-(tert.-butyl-dimethyl-silanyloxy)-3-hydroxy-hexyl]-3,7-dimethyl-1,2,3,7,8,8a-hexahydro-naphthalen-1-yl ester and 5.2 ml (37 mmol) triethyl amine in 22 ml DMSO is added a solution of 4.4 g (28 mmol) SO$_3$.pyridine complex in 22 ml DMSO. After 2 hours at room temperature the mixture is poured on ice and extracted twice with ethyl acetate. The combined organic phases are dried over sodium sulfate and the solvent evaporated. The residue is chromatographed over silica gel (hexane/ethyl acetate 9/1 to 7/3) to afford 2-methyl-butyric acid 8-[6-benzylcarbamoyl-5-(tert.-butyl-dimethyl-silanyloxy)-3-oxo-hexyl]-3,7-dimethyl-1,2,3,7,8,8a-hexahydro-naphthalen-1-yl ester as an oil. MS (FAB) m/z 630 ([M+Li]$^+$).

To a stirred solution of 200 mg (0.32 mmol) 2-methyl-butyric acid 8-[6-benzylcarbamoyl-5-(tert.-butyl-dimethyl-silanyloxy)-3-oxo-hexyl]-3,7-dimethyl-1,2,3,7,8,8a-hexahydro-naphthalen-1-yl ester in 5 ml methylene chloride are added 0.3 g (2.6 mmol) trifluoroacetic acid. After 2 hours at room temperature the reaction mixture is quenched with saturated aqeous sodium bicarbonate. The aqueous phase is separated and extracted twice with ethyl acetate. The combined organic phases are dried over sodium sulfate and the solvent is evaporated. The residue is chromatographed over silica gel (hexane/ethyl acetate 7/3 to 2/3) affording the title compound as a white powder foam. MS (FAB) m/z 480 ([M+Li]$^+$)

EXAMPLE 46

2-Methyl-butyric Acid 3,7-Dimethyl-8-[2-(6-oxo-1, 6-dihydro-pyridin-2-yl)-ethyl]-1,2,3,7,8,8a-hexahydro-naphthalen-1-yl Ester To a stirred solution of 1.0 g (1.9 mmol) 2-methyl-butyric acid 8-[5-(tert.-butyl-dimethyl-silanyloxy)-6-carbamoyl-3-oxo-hexyl]-3,7-dimethyl-1,2,3,7,8,8a-hexahydro-naphthalen-1-yl ester in 25 ml methylene chloride are added 0.7 g (6.5 mmol) trifluoroacetic acid. After 2 hours at room temperature the reaction mixture is quenched with saturated aqueous sodium bicarbonate. The aqueous phase is separated and extracted twice with ethyl acetate. The combined organic phases are dried over sodium sulfate and the solvent is evaporated. The residue is chromatographed over silica gel (hexane/acetone 1/1) to afford the title compound as a white foam. MS (FAB) n/z 384 ([M+H]$^+$)

EXAMPLE 47

2-Methyl-butyric Acid 3,7-Dimethyl-8-[2-(1-methyl-6-oxo-1,6-dihydro-pyridin-2-yl)-ethyl]-1,2,3, 7,8,8a-hexahydro-naphthalen-1-yl Ester To a stirred solution of 77 mg (0.2 mmol) 2-methyl-butyric acid 3,7-dimethyl-8-[2-(6-oxo-1,6-dihydro-pyridin-2-yl)-ethyl]-1,2,3,7,8,8a-hexahydro-naphthalen-1-yl ester in 5 ml DMF are added 0.1 g (0.8 mmol) potassium carbonate and 0.1 g (0.8 mmol) methyl iodide. After 2 hours at room temperature the mixture is poured on water. The aqueous phase is separated and extracted twice with ethyl acetate. The combined organic phases are dried over sodium sulfate and the solvent is evaporated in vacuo. The residue is chromatographed over silica gel eluting with hexane/acetone 1/1 to afford the title compound as white powder.

MS (FAB) m/z 404 ([M+Li]$^+$).

EXAMPLE 48

2-Ethyl-butyric Acid 8-[2-(1-Benzyl-6-oxo-1,6-dihydro-pyridin-2-yl)-ethyl]-3,7-dimethyl-1,2,3,7,8, 8a-hexahydro-naphthalen-1-yl Ester

MS(ESI): 487 M$^+$.

Compounds of e.g. Examples 6, 15 and 33 are preferred for the prevention or treatment of disorders or diseases mediated by LFA-1/ICAM-1 or ICAM-3 interactions, e.g. ischemia/reperfusion injury, chronic graft rejection. For example, in the Jurkat Cell Assay disclosed hereinbefore they have an IC$_{50}$ of 4, 2.2. and 1.2 μM, respectively. In the murine thioglycollate induced peritonitis model the compounds of e.g. Ex. 6 and 33 fully inhibit the neutrophil migration when administered s.c. at a dose of 1 and 0.1 mg/kg, respectively. It is therefore indicated that for the treatment or prevention of these disorders or diseases, the compounds may be administered to humans at a daily dosage from 5 to 750 mg.

What is claimed is:

1. A compound of formula II

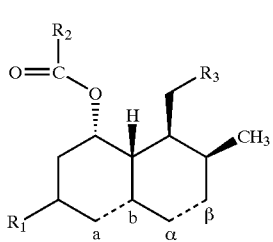

wherein $R_1$ is ⋯H, ⋯$C_{1-4}$alkyl or ◂—$OR_a$;

$R_a$ is H; $C_{1-6}$ alkyl; $C_{1-6}$ alkyl substituted by OH or $C_{1-4}$ alkyoxy; $C_{2-6}$ alkenyl; or aryl-$C_{1-4}$ alkyl;

$R_2$ is $C_{1-8}$alkyl, $C_{3-7}$cycloalkyl, aryl, heteroaryl, $C_{3-7}$cycloalkyl-$C_{1-4}$alkyl, aryl-$C_{1-4}$alkyl or heteroaryl-$C_{1-4}$alkyl;

$R_3$ is a radical of formula (i), (ii), (iii) or (iv)

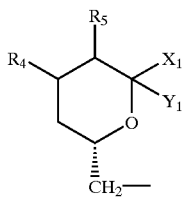 (i)

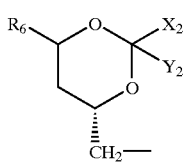 (ii)

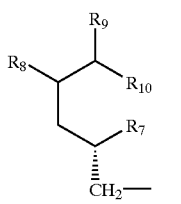 or (iii)

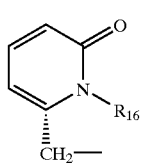 (iv)

wherein $X_1$ and $Y_1$ are (H,H), (H,OH) or =O;

$X_2$ and $Y_2$ are =O or (R,R) wherein each R independently is H, $C_{1-3}$ alkyl, substituted $C_{1-3}$ alkyl or $X_2$ and $Y_2$ form together with the carbon atom to which they are bound a 4-, 5-, 6- or 7-membered carbo- or heterocyclic ring, $R_4$ is $OR_a$ wherein $R_a$ is as defined above; or —O—$COR_b$ wherein $R_b$ is $C_{1-8}$ alkyl optionally substituted by OH, $C_{3-7}$ cycloalkyl, $C_{3-7}$ cycloalkyl-$C_{1-4}$alkyl, aryl, aryl-$C_{1-4}$ alkyl, heteroalkyl, heteroaryl or heteroaryl-$C_{1-4}$ alkyl; or $NR_cR_d$ wherein each of $R_c$ and $R_d$, independently, is $C_{1-6}$alkyl or form together with the nitrogen to which they are bound a heterocyclic ring optionally comprising an oxygen or another nitrogen atom;

$R_5$ is H, $C_{1-4}$ alkyl, $C_{3-9}$ alkenyl, $C_{3-9}$ alkynyl, aryl-$C_{1-4}$ alkyl or $C_{3-7}$ cycloalkyl-$C_{1-4}$ alkyl;

$R_6$ is —$CHR_{11}$—CO—$NR_{12}R_{13}$ wherein $R_{11}$ is $R_5$ and each $R_{12}$ and $R_{13}$, independently, is H, $C_{1-4}$ alkyl, or substituted $C_{1-4}$ alkyl;

$R_7$ is =O or (H,OH);

$R_8$ is $OR_a$; or $NR_eR_f$ wherein each of $R_e$ and $R_f$, independently, is H, $C_{1-6}$alkyl, $C_{1-6}$alkyl substituted by OH or $C_{1-4}$alkoxy, or a 5-membered heterocyclic ring;

or $R_7$ and $R_8$, together, form a dioxy-$C_{1-4}$alkylene group or —O—CO—O—;

$R_9$ is $R_5$;

$R_{10}$ is $COOR_a$; $CH_2OR_c$ wherein $R_c$ is $R_a$ or $COR_b$; or $CONR_{14}R_{15}$ or $CH_2NR_{14}R_{15}$ wherein each of $R_{14}$ and $R_{15}$ independently is $C_{1-4}$alkyl, hydroxy substituted $C_{1-4}$alkyl, carbamoyl-methyl, ($C_{1-4}$alkyl)-carbamoyl-methyl or di($C_{1-4}$alkyl)-carbamoyl-methyl, or one of $R_{14}$ and $R_{15}$ is hydrogen and the other is $C_{1-6}$alkyl, $C_{1-6}$alkyl substituted by OH and/or a group selected from carbamoyl, ($C_{1-4}$alkyl)-carbamoyl, di($C_{1-4}$alkyl)-carbamoyl and heteroaryl-$C_{1-4}$alkyl, $C_{1-6}$alkoxy-carbonyl-methyl, adamantyl-methyl, $C_{3-7}$cycloalkyl-$C_{1-4}$alkyl, aryl-$C_{1-4}$alkyl wherein aryl may be substituted and $C_{1-4}$alkyl may be substituted by carbamoyl or $C_{1-4}$alkoxy-carbonyl, or heteroaryl-$C_{1-4}$alkyl wherein heteroaryl may be substituted by carbamoyl or $C_{1-4}$alkoxy-carbonyl and $C_{1-4}$alkyl may be substituted by carbamoyl, or $R_{14}$ and $R_{15}$ form together with the nitrogen to which they are attached a heterocyclic ring optionally consisting of a further nitrogen atom and optionally substituted by $C_{1-4}$alkyl, ($C_{1-4}$alkoxy)-carbonyl, carbamoyl, dioxy-$C_{1-4}$alkylene, aryl-$C_{1-4}$alkyl or heteroaryl wherein heteroaryl may be substituted by $C_{1-4}$alkoxy-carbonyl;

$R^{16}$ is H; $C_{1-4}$alkyl; aryl-$C_{1-4}$alkyl wherein aryl may be substituted by halogen, OH, amino optionally substituted, COOH, $CF_3$, $C_{1-4}$ alkoxy or cyano; or $C_{3-7}$cycloalkyl-$C_{1-4}$aryl;

each of a-b and α-β, independently, is either a single bond or a double bond, in free form or in a pharmaceutically acceptable salt form provided that 1) $R_4$ is other than $OR_a$ when $R_3$ is a radical of formula (i) wherein $X_1$ and $Y_1$ are (H,H), (H,OH) or =O, 2) $R_8$ is other than $OR_a$ when $R_3$ is a radical of formula (iii) wherein $R_{10}$ is $COOR_a$ and $R_7$ is (H,OH), 3) $R_{10}$ is other than $CH_2OR_a$ when $R_3$ is a radical of formula (iii) wherein $R_7$ and $R_8$ form together a dioxy $C_{1-4}$ alkylene group and $R_9$ is H, or 4) One of $R_{14}$ and $R_{15}$ is other than aryl $C_{1-4}$ alkyl wherein $C_{1-4}$ alkyl is substituted by $C_{1-4}$ alkoxy-carbonyl, the other of $R_{14}$ and $R_{15}$ being H, when $R_3$ is a radical of formula (iii) wherein $R_{10}$ is $CONR_{14}R_{15}$.

2. A compound according to claim 1, wherein $R_1$ is H or $CH_3$; $R_2$ is $C_{4-8}$alkyl and $R_3$ is a radical of formula (iii) wherein $R_9$ is other than H and $R_{10}$ is other than $COOR_a$.

3. A pharmaceutical composition comprising a compound according to claim 1, in free form or in pharmaceutically acceptable salt form and a pharmaceutically acceptable diluent or carrier therefor.

4. A method for treating and/or preventing chronic rejection of organ and tissue allo- or xenografts comprising administering to a subject in need thereof an effective amount of a compound which is an LFA-1 inhibitor which binds to the south pole pocket of LFA-1 I-domain, wherein the compound inhibits HMG CoA R activity with an $IC_{50}$ of $\geq 1$ μM in the InVitro Microsomal Assay of HMG CoA R Inhibition.

5. A method according to claim 4, wherein the south pole pocket of LFA-1 I-domain is defined by the amino acids: Val 130, Leu 132, Phe 134, Phe 153, Val 157, Leu 161, Tyr 166, Thr 231, Val 233, Ile 235, Tyr 257, Ile 259, Lys 287, Glu 301, Leu 302 and Lys 305.

6. A method according to claim 5, wherein the compound is a mevinolin.

7. A method according to claim 5, wherein the compound interacts with said south pole pocket within a distance of <5 Å.

8. A method according to claim 5, wherein the compound interacts with said south pole pocket within a distance of 4–4.5 Å.

9. A method according to claim 5, wherein the compound inhibits adhesion of Jurkat or Hut 78 cells to ICAM-1 with an IC50 of ≦30 μM.

10. A method for treating autoimmune diseases, acute or chronic inflammatory diseases, ischemia/reperfusion injury, or infectious diseases, or for treating and/or preventing acute or chronic rejection of organ or tissue allo- or xeno-grafts, comprising administering to a subject in need thereof an effective amount of a mevinolin compound of formula I

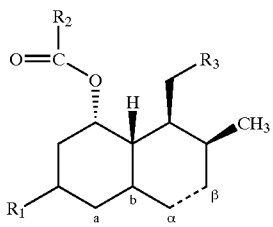

I wherein $R_1$ is ·····''''H, ·····'''$C_{1-4}$alkyl or ◂━━$OR_a$;

$R_a$ is H; $C_{1-6}$ alkyl; $C_{1-6}$ alkyl substituted by OH or $C_{1-4}$ alkyoxy; $C_{2-6}$ alkenyl; or aryl-$C_{1-4}$ alkyl;

$R_2$ is $C_{1-8}$alkyl, $C_{3-7}$cycloalkyl, aryl, heteroaryl, $C_{3-7}$cycloalkyl-$C_{1-4}$alkyl, aryl-$C_{1-4}$alkyl or heteroaryl-$C_{1-4}$alkyl;

$R_3$ is a radical of formula (i), (ii), (iii) or (iv)

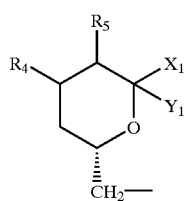

(i)

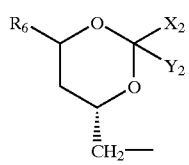

(ii)

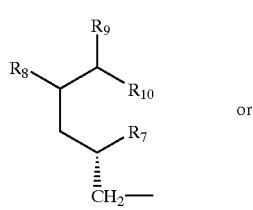

(iii)

or

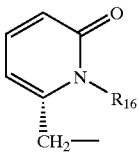

(iv)

wherein $X_1$ and $Y_1$ are (H,H), (H,OH) or =O;

$X_2$ and $Y_2$ are =O or (R,R) wherein each R independently is H, $C_{1-3}$ alkyl, substituted $C_{1-3}$ alkyl or $X_2$ and $Y_2$ form together with the carbon atom to which they are bound a 4-, 5-, 6- or 7-membered carbo- or heterocyclic ring, $R_4$ is $OR_a$ wherein $R_a$ is as defined above; or —O—$COR_b$ wherein $R_b$ is $C_{1-8}$ alkyl optionally substituted by OH, $C_{3-7}$ cycloalkyl, $C_{3-7}$ cycloalkyl-$C_{1-4}$alkyl, aryl, aryl-$C_{1-4}$ alkyl, heteroalkyl, heteroaryl or heteroaryl-$C_{1-4}$ alkyl; or $NR_cR_d$ wherein each of $R_c$ and $R_d$, independently, is $C_{1-6}$alkyl or form together with the nitrogen to which they are bound a heterocyclic ring optionally comprising an oxygen or another nitrogen atom;

$R_5$ is H, $C_{1-4}$ alkyl, $C_{3-9}$ alkenyl, $C_{3-9}$ alkynyl, aryl-$C_{1-4}$ alkyl or $C_{3-7}$ cycloalkyl -$C_{1-4}$alkyl;

$R_6$ is —$CHR_{11}$—CO—$NR_{12}R_{13}$ wherein $R_{11}$ is $R_5$ and each $R_{12}$ and $R_{13}$, independently, is H, $C_{1-4}$ alkyl, or substituted $C_{1-4}$ alkyl;

$R_7$ is =O or (H,OH);

$R_8$ is $OR_a$; or $NR_eR_f$ wherein each of $R_e$ and $R_f$, independently, is H, $C_{1-6}$alkyl, $C_{1-6}$alkyl substituted by OH or $C_{1-4}$alkoxy, or a 5-membered heterocyclic ring;

or $R_7$ and $R_8$, together, form a dioxy-$C_{1-4}$alkylene group or —O—CO—O—;

$R_9$ is $R_5$;

$R_{10}$ is $COOR_a$; $CH_2OR_c$ wherein $R_c$ is $R_a$ or $COR_b$; or $CONR_{14}R_{15}$ or $CH_2NR_{14}R_{15}$ wherein each of $R_{14}$ and $R_{15}$ independently is $C_{1-4}$alkyl, hydroxy substituted $C_{1-4}$alkyl, carbamoyl-methyl, ($C_{1-4}$alkyl)-carbamoyl-methyl or di($C_{1-4}$alkyl)-carbamoyl-methyl, or one of $R_{14}$ and $R_{15}$ is hydrogen and the other is $C_{1-6}$alkyl, $C_{1-6}$alkyl substituted by OH and/or a group selected from carbamoyl, ($C_{1-4}$alkyl)-carbamoyl, di($C_{1-4}$alkyl)-carbamoyl and heteroaryl-$C_{1-4}$alkyl, $C_{1-6}$alkoxy-carbonyl-methyl, adamantyl-methyl, $C_{3-7}$cycloalkyl-$C_{1-4}$alkyl, aryl-$C_{1-4}$alkyl wherein aryl may be substituted and $C_{1-4}$alkyl may be substituted by carbamoyl or $C_{1-4}$alkoxy-carbonyl, or heteroaryl-$C_{1-4}$ alkyl wherein heteroaryl may be substituted by carbamoyl or $C_{1-4}$alkoxy-carbonyl and $C_{1-4}$alkyl may be substituted by carbamoyl, or $R_{14}$ and $R_{15}$ form together with the nitrogen to which they are attached a heterocyclic ring optionally consisting of a further nitrogen atom and optionally substituted by $C_{1-4}$alkyl, ($C_{1-4}$alkoxy)-carbonyl, carbamoyl, dioxy-$C_{1-4}$alkylene, aryl-$C_{1-4}$alkyl or heteroaryl wherein heteroaryl may be substituted by $C_{1-4}$alkoxy-carbonyl;

$R^{16}$ is H; $C_{1-4}$alkyl; aryl-$C_{1-4}$alkyl wherein aryl may be substituted by halogen, OH, amino optionally substituted, COOH, $CF_3$, $C_{1-4}$ alkoxy or cyano; or $C_{3-7}$cycloalkyl-$C_{1-4}$aryl; each of a-b and α-β, independently, is either a single bond or a double bond, in free form or in a pharmaceutically acceptable salt form.

11. A method according to claim 10, wherein $R_1$ is H or $CH_3$; $R_2$ is $C_{4-8}$alkyl; and $R_3$ is a radical of formula (i), (iii) or (iv) as defined in claim 10.

* * * * *